(12) United States Patent
Buchalova et al.

(10) Patent No.: US 11,452,693 B2
(45) Date of Patent: Sep. 27, 2022

(54) FREEZE DRIED ACTIVE COMPOSITION AND A SYSTEM FOR USING THE SAME

(71) Applicant: Conopco, Inc., Englewood Cliffs, NJ (US)

(72) Inventors: Maria Buchalova, Sandy Hook, CT (US); Teanoosh Moaddel, Watertown, CT (US); Ravi Krishnan, Mumbai (IN); Lise Jorgensen, Denville, NJ (US); Krassimir Petkov Velikov, Utrecht (NL); Michael Jacobus Suijker, JD Schiedam (NL)

(*) Notice: Subject to any disclaimer, the term of this patent is extended or adjusted under 35 U.S.C. 154(b) by 0 days.

(21) Appl. No.: 16/629,708

(22) PCT Filed: Jun. 21, 2018

(86) PCT No.: PCT/EP2018/066642
§ 371 (c)(1),
(2) Date: Jan. 9, 2020

(87) PCT Pub. No.: WO2019/011620
PCT Pub. Date: Jan. 17, 2019

(65) Prior Publication Data
US 2020/0170953 A1  Jun. 4, 2020

(30) Foreign Application Priority Data
Jul. 12, 2017  (WO) ............... PCT/CN2018/092606

(51) Int. Cl.
| A61K 31/203 | (2006.01) |
| A61K 9/19 | (2006.01) |
| A61K 9/107 | (2006.01) |
| A61K 31/05 | (2006.01) |
| A61K 31/375 | (2006.01) |
| A61K 31/455 | (2006.01) |
| A61K 31/717 | (2006.01) |

(52) U.S. Cl.
CPC ............ *A61K 9/19* (2013.01); *A61K 9/107* (2013.01); *A61K 31/05* (2013.01); *A61K 31/203* (2013.01); *A61K 31/375* (2013.01); *A61K 31/455* (2013.01); *A61K 31/717* (2013.01)

(58) Field of Classification Search
CPC ................... A61K 9/19; A61K 31/203
See application file for complete search history.

(56) References Cited

U.S. PATENT DOCUMENTS

| 2009/0304609 A1 | 12/2009 | Allemand et al. |
| 2010/0226982 A1 | 9/2010 | Malessa |
| 2010/0272699 A1 | 10/2010 | Pain et al. |
| 2010/0273747 A1 | 10/2010 | Malessa et al. |
| 2015/0314004 A1 | 11/2015 | Li |
| 2016/0000669 A1 | 1/2016 | Hinman et al. |
| 2019/0151228 A1* | 5/2019 | Berry ............... A61P 17/00 |

FOREIGN PATENT DOCUMENTS

| CN | 1553794 | 12/2004 | |
| CN | 105663144 A * | 6/2016 | |
| JP | 2004527471 | 9/2004 | |
| WO | WO0182866 | 11/2001 | |
| WO | WO02053089 | 9/2004 | |
| WO | WO2008086724 | 7/2008 | |
| WO | WO2012122678 | 9/2012 | |
| WO | WO2014101743 | 7/2014 | |
| WO | WO2014121733 | 8/2014 | |
| WO | WO2014206137 | 12/2014 | |
| WO | WO2015032319 | 3/2015 | |
| WO | WO-2015059001 A * | 4/2015 | ........ A61K 8/4926 |
| WO | WO2015074587 | 5/2015 | |
| WO | WO2017042049 | 3/2017 | |

OTHER PUBLICATIONS

IPRP2 in PCTEP2018066642; Oct. 16, 2019.
Search Report and Written Opinion in PCTEP2018066642.
Search Report and Written Opinion in EP17187892; dated Feb. 23, 2018.
M. Alpbaz et al.; The Measurement of Interfacial Tension By Drop-Weight Method; Commun. Fac. Sci. Univ. Ank. Serie B; 1988; pp. 103-112; vol. 34;.
Kalia et al.; Nanofibrillated cellulose: surface modification and potential applications; Colloid Polymer Science; 2014; pp. 5-31; vol. 292; .
Written Opinion 2 in PCTEP2018066642; dated Jun. 13, 2019.
Zasada et al; Adv Dermatol Allergol; 2019; 392-397; XXXVI.

* cited by examiner

*Primary Examiner* — Benjamin J Packard
(74) *Attorney, Agent, or Firm* — Edward A. Squillante, Jr.

(57) ABSTRACT

Freeze dried active compositions are described. The compositions comprise less than 6.5% by weight water and they may be hydrated or added to end use compositions in order to yield compositions for delivering superior topical benefits to consumers.

19 Claims, No Drawings

FREEZE DRIED ACTIVE COMPOSITION AND A SYSTEM FOR USING THE SAME

FIELD OF THE INVENTION

The present invention is directed to a freeze dried active composition and a system for using the same. More particularly, the freeze dried active composition of the present invention originates from an emulsion that can be rehydrated for end use or added to an end use composition to boost the benefits of the same. The freeze dried active composition of the present invention comprises an oil to active weight ratio of at least 4:1 and is surprisingly stable for ease of rehydrating and addition to an end use composition.

BACKGROUND OF THE INVENTION

Many consumers find it desirable to deliver skin benefits via methods that rely on the application of topical compositions. This is especially true when consumers wish, for example, to look younger by reducing facial lines and wrinkles as well as blotchy color marks on the skin.

Minimizing cutaneous aging, both intrinsic and from photoaging, is often attempted with compositions having actives like retinoids and resorcinols. While such compositions can provide benefits to skin, certain skin actives can be unstable, resulting in poor composition performance when the composition is topically applied by a consumer. This is particularly true when, for example, retinoids and resorcinols are the actives of choice. Individually, both provide excellent skin benefits but together they are typically incompatible when formulated in the same composition. Such incompatibility renders the actives less effective, causing consumer disappointment and often the need to use additional amounts of composition. Additional uses are not desired from a consumer convenience and cost point of view and when marketing products in an environment very concerned about waste and a sustainable living plan.

It is of increasing interest to develop skin benefit compositions with stable actives for maximum consumer benefit while at the same time being conscious of working towards a zero environmental footprint. This invention, therefore, is directed to a freeze dried active composition and a system for using the same. The freeze dried active composition is suitable for hydration to produce an end use composition. The freeze dried active composition can be added to end use compositions to boost the benefits of the same. Such a composition can also be shipped in large quantities to points of distribution for energy efficient manufacturing benefits.
Additional Information Efforts have been disclosed for making freeze dry compositions. In U.S. Patent Application Nos. 2009/304609, 2010/0226982 A1 and 2010/0272699 A1 described are compositions obtained by freeze drying.

Other efforts have been disclosed for making freeze dried compositions. In WO 01/82866 A1, freeze dried compositions are described.

None of the additional information describes a freeze dried composition as claimed in the present invention.

SUMMARY OF THE INVENTION

In a first aspect, the present invention is directed to a freeze dried active composition comprising:
(a) active;
(b) oil;
(c) water;
(d) emulsifier; and
(e) thickening agent
wherein from 4 to 25 times more oil by weight is present than active in the composition, the oil having a peroxide value from 0 to 4 meq/kg and a polarity index of from 0.1 to 80 mN/m and less than 0.5% by weight of the total weight of oil in the freeze dried active composition is hydroxylated.

In a second aspect, the present invention is directed to a system and method whereby the system and method utilize the freeze dried active composition of the first aspect of this invention to boost performance of an end use composition.

In a third aspect, the present invention is directed to a system and method for rehydrating the freeze dry composition of the first aspect of this invention to produce an end use composition for personal use or in manufacturing.

All additional aspects of the present invention will more readily become apparent from the description and examples which follow.

Skin, as used herein, is meant to include skin on the arms, face, feet, neck, chest, hands, legs, buttocks and scalp (including hair). The freeze dried active composition (FDAC) of this invention is defined to mean a composition that may be rehydrated to produce an end use composition or added to an end use composition (oil or water continuous) for rehydration and to boost (i.e., enhance) the performance of the end use composition. However hydrated, the freeze dried active composition of this invention is meant to be one that after hydration delivers a benefit to skin after being topically applied. End use composition (water or oil continuous but preferably water continuous) is a composition for topical application and includes a cream, lotion, balm, serum, gel, mousse, aerosol or liquid deodorant or antiperspirant, shampoo, conditioner, liquid make-up and liquid personal wash. Active means an ingredient that improves a skin characteristic. FDAC emulsion precursor means the emulsion freeze-dried to yield the FDAC. Polarity index means the value measured of the interfacial tension of an oil taken against water and measured via the drop weight method (M. Alpbaz et al: The Measurement of Interfacial Tension by Drop Weight Method, Commun. Fac. Sci. Univ. Ank. Serie B, V 34, p 103, 1988). Peroxide value is a normal oxidation index of an oil as measured by standard iodometric titration. Actives not compatible means when present, their combined benefit is inferior to the benefit each provides alone. Retinoic acid precursor is defined to mean a component that, when oxidized, can convert to retinoic acid.

Unless explicitly stated otherwise, all ranges described herein are meant to include all ranges subsumed therein. The term comprising is meant to encompass the terms consisting essentially of and consisting of. For the avoidance of doubt, a composition comprising the FDAC of this invention is meant to include a composition consisting essentially of the same and a composition consisting of the same. Stable emulsion, as used herein, means an emulsion that does not phase separate prior to freeze drying where the emulsion preferably has a water continuous phase. All percentages used herein are meant to be by weight unless stated otherwise. Except in the operating comparative examples, or where otherwise explicitly indicated, all numbers in this description indicating amounts or ratios of materials or conditions and/or physical properties of materials and/or use are to be understood as modified by the word "about".

DETAILED DESCRIPTION OF THE INVENTION

The only limitation with respect to the active that may be used in the FDAC of this invention is that the same provides a benefit to skin when topically applied.

Illustrative examples of the actives suitable for use in this invention include those which are oil soluble like Vitamin A, D, E and K (and their oil soluble derivatives), sunscreens like ethylhexylmethoxycinnamate, bis-ethyl hexyloxyphenol methoxyphenol triazine, 2-ethylhexyl-2-cyano-3,3-diphenyl-2-propanoic acid, drometrizole trisiloxane, 3,3,5-trimethyl cyclohexyl 2-hydroxybenzoate, 2-ethylhexyl-2-hydroxybenzoate or mixtures thereof.

Additional oil soluble actives suitable for use include resorcinols like 4-ethyl resorcinol, 4-hexyl resorcinol, 4-phenylethyl resorcinol, 4-cyclopentyl resorcinol, 4-cyclohexyl resorcinol 4-isopropyl resorcinol or mixture thereof. Also, 5-substituted resorcinols like 4-cyclohexyl-5 methylbenzene-1,3-diol, 4-isopropyl-5-methylbenzene-1,3-diol, mixtures thereof or the like may be used. The 5-substituted resorcinols, and their synthesis are described in commonly assigned U.S. Published Patent Application No. 2016/0000669A1.

Even other oil soluble actives suitable for use include omega-3 fatty acids, omega-6 fatty acids, climbazole, farnesol, ursolic acid, myristic acid, geranyl geraniol, oleyl betaine, cocoyl hydroxyethyl imidazoline, hexanoyl sphingosine, 12-hydroxystearic acid, petroselinic acid, conjugated linoleic acid, terpineol, thymol mixtures thereof or the like.

In an especially preferred embodiment, the oil soluble active used in this invention is a retinoic acid precursor represented by the formula:

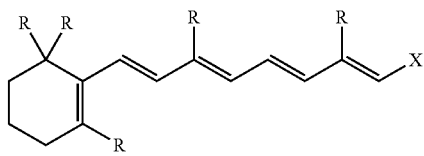

where each R is independently a hydrogen or a $C_{1-6}$ alkyl group and X is

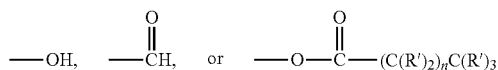

and further where each R' is hydrogen or a $C_1$-$C_3$ alkyl and n is an integer from 0 to 16 (preferably, 1 to 5).

Preferably, each R is $CH_3$, each R' is hydrogen, n is 1 and the retinoic acid precursor is retinol, retinal, retinyl propionate, retinyl palmitate, retinyl acetate or a mixture thereof,

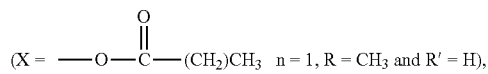

is typically preferred.

Still another retinoic acid precursor suitable for use is hydroxyanasatil retinoate made commercially available under the name Retextra® as supplied by Molecular Design International. The same may be used in a mixture with the actives described herein.

It is within the scope of this invention for the first and second active to be present in the FDAC at a weight ratio of 1:0.25 to 0.25:1 and typically at a weight ratio of 1.3:1 to 1:1.3.

In a preferred embodiment, when the FDAC comprises a first active, like a retinoic acid precursor, and a second active not compatible with the first active, like resorcinol, from 2 to 5, and preferably from 3 to 7, and most preferably, from 4 to 10 times more (by weight) of one is used over the other.

In another preferred embodiment, less than 0.3% by weight, and preferably, less than 0.1% by weight, and most preferably, no second active, like resorcinol, is present in the FDAC when the first active, like a retinoic acid precursor, is present, based on total weight of the FDAC and when the first and second active are not compatible with each other in the same composition.

In still another preferred embodiment, less than 0.3% by weight, and preferably, less than 0.1% by weight, and most preferably, no first active, like a retinoic acid precursor, is present when a second active, like resorcinol, is present, based on total weight of the FDAC and when the first and second active are not compatible with each other in the same composition.

Typically, the amount of oil soluble active used in this invention is from 0.001 to 10%, and preferably, from 0.01 to 6%, and most preferably, from 0.05 to 4.5% by weight, based on total weight of FDAC emulsion precursor and including all ranges subsumed therein.

The FDAC emulsion precursor (most preferably, water continuous) often has from 25 to 92%, and preferably, from 40 to 88%, and most preferably, from 55 to 88% by weight water, based on total weight of the FDAC emulsion precursor and including all ranges subsumed therein.

Oils (i.e., carrier for oil soluble active) suitable for use in this invention include those having a peroxide value from 0 to 4, and preferably, from 0.0 to 3.5, and most preferably, from 0.0 to 2.25. Such oils will also have a polarity index from 0.1 to 80 mN/m, and preferably, from 1.0 to 75 mN/m, and most preferably, from 10 to 70 mN/m.

Illustrative examples of oils suitable for use in this invention include hydrocarbons and polymer oils like mineral oil, squalane, squalene, isohexadecane or hydrogenated polyisobutene; and silicone oils like dimethicone or cyclomethicone; and esters like isopropyl myristate, isopropyl palmitate, isopropyl isostearate, isostearyl palmitate, isostearyl myristate, isostearyl isostearate, oleyl oleate, decyl oleate, decylcocoate, ethylhexylhydroxystearate, ethylhexyl palmitate, ethylhexyl stearate, cetearyl ethylhexanoate, cetearyl isononanoate, propylene glycol dicaprylate/dicaprate or caprylic capric triglyceride. Mixtures of the above oils may be used, but an often preferred oil (based on total weight of oil) is one comprising at least 50%, and preferably, at least 75%, and most preferably, all caprylic capric triglyceride.

Typically 4 to 25 times more oil is used than active, and preferably 4.5 to 25 times more oil, and most preferably, from 5 to 25 times more oil by weight is used than active, including all ranges subsumed therein. Oil typically makes up from 5 to 75, and preferably, from 6 to 50, and most preferably from 7 to 20% by weight of the FDAC emulsion precursor, including all ranges subsumed therein.

The emulsifiers suitable for use in this invention typically have an HLB from 5 to 20, and preferably, from 7 to 18, and most preferably from 8 to 16, including all ranges subsumed therein. Illustrative examples of the types of emulsifiers suitable for use in the FDAC and FDAC emulsion precursor described in this invention include ceteareth-20, cetearyl glucoside, ceteth-10, ceteth-20, isosteareth lauramide, lecithin, linoeamide, oleth-10, methyl glucose sesquistearate, polysorbate 20, polysorbate 40, polysorbate 60, polysorbate 80, polysorbate 85, stearamide MEA, mixtures thereof or the like.

Emulsifiers sold under the names Tween®, Alkest® and Canarcel® are typically preferred. Tween® 40 (Sigma-Aldrich), polyoxyethylene sorbitan monopalmitate, is especially preferred as the emulsifier.

Emulsifiers typically make up from 0.1 to 25%, and preferably, from 0.5 to 20%, and most preferably, from 0.8 to 5% by weight of the FDAC emulsion precursor, including all ranges subsumed therein.

Preservatives can desirably be incorporated into the FDAC emulsion precursor (and therefore, the resulting FDAC) of this invention to protect against the growth of potentially harmful microorganisms, although it is within the scope of the invention for the FDAC emulsion precursor and FDAC to be preservative free. Suitable traditional preservatives for compositions of this invention are alkyl esters of para-hydroxybenzoic acid. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are iodopropynyl butyl carbamate, phenoxyethanol, 1,2-octanediol, hydroxyacetophenone, ethylhexylglycerine, hexylene glycol, methyl paraben, propyl paraben, imidazolidinyl urea, sodium dehydroacetate and benzyl alcohol. The preservatives should be selected having regard for the use of the composition and possible incompatibilities between the preservatives and other ingredients in the emulsion. Preservatives are preferably employed in amounts ranging from 0.01% to 2% by weight in the FDAC emulsion precursor, including all ranges subsumed therein. Combinations of 1,2-octanediol and phenoxyethanol, or iodopropynyl butyl carbamate and phenoxyethanol are preferred, with phenoxyethanol and 1,2-octanediol, collectively, making up less than 0.5% by weight of the total weight of the FDAC emulsion precursor of the present invention. Also preferred is a preservative system with hydroxyacetophenone alone or in a mixture with other preservatives.

Thickening agents are included in the FDAC precursor emulsion of the present invention. Particularly useful are the polysaccharides. Examples include fibers, starches, natural/synthetic gums and cellulosics. Representative of the starches are chemically modified starches such as sodium hydroxypropyl starch phosphate and aluminum starch octenylsuccinate. Tapioca starch is often preferred, as is maltodextrin. Suitable gums include xanthan, sclerotium, pectin, karaya, arabic, agar, guar (including Acacia senegal guar), carrageenan, alginate and combinations thereof. Suitable cellulosics include hydroxypropyl cellulose, hydroxypropyl methylcellulose, ethylcellulose, sodium carboxy methylcellulose (cellulose gum/carboxymethyl cellulose) and cellulose (e.g. cellulose microfibrils, cellulose nanocrystals or microcrystalline cellulose). Sources of cellulose microfibrils include secondary cell wall materials (e.g. wood pulp, cotton), bacterial cellulose, and primary cell wall materials. Preferably the source of primary cell wall material is selected from parenchymal tissue from fruits, roots, bulbs, tubers, seeds, leaves and combination thereof; more preferably is selected from citrus fruit, tomato fruit, peach fruit, pumpkin fruit, kiwi fruit, apple fruit, mango fruit, sugar beet, beet root, turnip, parsnip, maize, oat, wheat, peas and combinations thereof; and even more preferably is selected from citrus fruit, tomato fruit and combinations thereof. A most preferred source of primary cell wall material is parenchymal tissue from citrus fruit. Citrus fibers, such as those made available by Herbacel® as AQ Plus can also be used as source for cellulose microfibrils. The cellulose sources can be surface modified by any of the known methods including those described in Colloidal Polymer Science, Kalia et al., "Nanofibrillated cellulose: surface modification and potential applications" (2014), Vol 292, Pages 5-31.

Synthetic polymers are yet another class of effective thickening agent. This category includes crosslinked polyacrylates such as the Carbomers, polyacrylamides such as Sepigel 305 and taurate copolymers such as Simulgel EG and Arlstoflex AVC, the copolymers being identified by respective INCI nomenclature as Sodium Acrylate/Sodium Acryloyldimethyl Taurate and Acryloyl Dimethyltaurate/Vinyl Pyrrolidone Copolymer. Another preferred synthetic polymer suitable for thickening is an acrylate-based polymer made commercially available by Seppic and sold under the name Simulgel INS100. Calcium carbonate, fumed silica, and magnesium-aluminum-silicate may also be used.

Amounts of the thickening agent, when used, may range from 0.001 to 22%, and preferably, from 0.1 to 17%, and most preferably, from 0.2 to 16% by weight of the composition, based on total weight of the FDAC emulsion precursor and including all ranges subsumed therein. Maltodextrin, xanthan gum, and carboxymethyl cellulose are the often preferred thickening agents used, typically with 4 to 15, and preferably, 10 to 16 times more maltodextrin than carboxymethyl cellulose being used. Thickening agent typically makes up from 4 to 20%, and preferably, from 5 to 16%, and most preferably, from 8 to 12.5% by weight of the FDAC emulsion precursor including oil ranges subsumed therein.

Fragrances, fixatives and exfoliants may optionally be included in FDAC emulsion precursor of the present invention. Each of these substances may range from about 0.05 to about 5%, preferably between 0.1 and 3% by weight.

Conventional humectants may optionally be employed as additives to the FDAC emulsion precursor of the present invention as a skin benefit agent. These are generally polyhydric alcohol type materials. Typical polyhydric alcohols include glycerol (i.e., glycerine or glycerin), propylene glycol, dipropylene glycol, polypropylene glycol, polyethylene glycol, sorbitol, hydroxypropyl sorbitol, hexylene glycol, 1,3-butylene glycol, isoprene glycol, 1,2,6-hexanetriol, ethoxylated glycerol, propoxylated glycerol and mixtures thereof. Most preferred is glycerin, propylene glycol or a mixture thereof. The amount of humectant employed may range anywhere from 0.0 to 10 to 15% by weight of the total weight of oil present in the FDAC emulsion precursor.

FDAC emulsion precursors (and resulting FDAC) of the present invention may optionally include water soluble actives like Vitamin $B_2$, Vitamin $B_3$ (niacinamide), Vitamin $B_6$, Vitamin C and the like. Derivatives of the vitamins may also be employed. For instance, Vitamin C derivatives such as ascorbyl tetraisopalmitate, magnesium ascorbyl phosphate and ascorbyl glycoside may be used. Other water soluble actives suitable for use in the water/continuous phase of the FDAC emulsion precursor and FDAC include extracts like sage, aloe vera, green tea, grapeseed, thyme, chamomile, liquorice or rosemary extract or mixtures thereof. Still other water soluble actives suitable for use include alpha hydroxyacids like lactic and glycolic acid, beta hydroxy acids like salicylic acid, amino acids like cystine, arginine, lysine, glutamine, glycine, glutamic acid (and its derivatives, like pyroglutamic acid), alanine, valine and skin benefit agents like ferulic acid, hyaluronic acid, and allantoin. Water soluble sunscreens like ensulizole may also be used. Total amount of water soluble actives (including mixtures) when present in the FDAC emulsion precursors according to the present invention may range from 0.0 to 15%, preferably from 0.001 to 10%, optimally from 0.01 to 4% by weight based on total weight of the FDAC emulsion precursor and including all ranges subsumed therein.

When making the FDAC emulsion precursor of the present invention, the desired ingredients may be mixed to produce water and oil phases. The same may be mixed under moderate shear with emulsifier under atmospheric conditions with temperature being from ambient to 85° C. Use of a homogenizing system such as a Sonic Corporation Sonolator™ may also be used. Preferably, retinoids are protected from light and left in an inert gas (e.g. nitrogen, argon) atmosphere.

In a preferred embodiment, the resulting emulsion (FDAC emulsion precursor) has a viscosity from 750 to 55,000 cps, and preferably, from 2,000 to 40,000 cps, and most preferably, from 5,000 to 30,000 cps, including all ranges subsumed therein, where the viscosity of the FDAC emulsion precursor may be measured with a Brookfield (DV-1+) Viscometer, temperature 25° C. and set at 20 RPM, RV6 for 30 seconds.

The resulting FDAC emulsion precursor may be freeze dried (lyophilization) by any art recognized technique. Such a technique includes the steps of first freezing the FDAC emulsion precursor in a freezer at about −17 to −20° C. Optionally the precursor can be frozen in liquid nitrogen (about −200° C.) or in a mixture of acetone and dry ice (about −80° C.) by shell freezing in the round bottom flask. The shell freezing takes typically about half an hour to 1 hour. The freezing process is typically overnight and it is desirable to cover the FDAC emulsion precursor while it freezes.

The frozen FDAC emulsion precursors can then be transferred to a laboratory freeze dryer over the course of a 1 to 5 day period. Drying temperature is typically from 18° C. to 25° C. and cooling in a cooling unit is preferably carried out from −50° to −90° C. Vacuum of 0.07 to 1.8, and preferably, from 0.08 to 1.3 mbar is typically applied to drive off water such that the resulting FDAC is 6.5% or less, and preferably, from 0.001 to 4.5% or less, and most preferably, 0.01 to 3.85% by weight water, based on total weight of the FDAC and including all ranges subsumed therein. In an especially preferred embodiment, the FDAC of this invention is less than 1% by weight water. When vacuum is applied, it is preferred that a portion of the cover (if used) on the FDAC emulsion precursor is removed before the actual drying step is started.

The shape or form of the resulting FDAC is dependent on the shape and size of the container or form carrying or holding the FDAC emulsion precursor during the freeze drying process. Large batches, typically powders, may be made when the FDAC is used as the basis to make end use composition in manufacturing and after hydration. Such powders may be made by freeze drying emulsion spread over a large surface. Large surface freeze drying can result in flakes which may be subjected to, for example, vibration, shear and/or tumbling to produce powder. The FDAC in powder form may also be sold directly to consumers for hydration at the time of use or for adding to an already existing end use composition. The amount of FDAC and water, end use product or both used would be a function of how viscous of a product the consumer desires upon hydration as well as how much boosting a consumer would want to do (or is instructed to do) to an already existing end use product. Often, a manufacturer would be instructed to use from 2 to 30%, and preferably, from 10 to 25%, and most preferably, from 10 to 20% by weight more water than FDAC of the present invention when manufacturing in order to produce end use composition for sale directly to consumer for use. A consumer would be instructed to use 2 to 30%, and preferably, from 10 to 25%, and most preferably, from 10 to 20% by weight more water and/or end use composition when either making end use product by shearing in his or her hands or when boosting already existing end use product to yield an enhanced end use composition.

It is also within the scope of this invention to prepare FDAC in capsule or tablet form. Such forms are a function of the container used during the freeze dry process. Capsule and tablet formats of FDAC may be used in the manner described for powders.

In a preferred embodiment, when the FDAC of this invention is used to boost the performance of an end use composition. The end use composition will preferably be formulated with a resorcinol and the FDAC will preferably comprise at least one retinoic acid precursor or vice versa. The combination of the two unexpectedly results in a superior product for delivering skin benefits to a consumer upon topical application.

The equipment used to freeze dry the FDAC emulsion precursors of this invention is commercially available and typically sold under the names CD12, Hetosic, Denmark and Millrock Technology. Benchtop and Console equipment may be employed.

The packaging for the FDAC of this invention is typically a bottle with small orifices to shake out the FDAC. Such a package is typically desired when the FDAC is a powder or flake. When a capsule or tablet, the FDAC may be dispensed from an art recognized jar, box or blister pack. Product (FDAC) size will be consistent with dosing/use instructions for the consumer. The packaging employed may also comprise art recognized and customary dosing capabilities.

The end use compositions suitable for boosting with FDAC of this invention are limited only to the extent that they may be topically applied to provide a consumer benefit. Superior products made commercially available by Unilever® under the brand names Dove®, Ponds®, Simple®, Vaseline®, Fair and Lovely®, St Ives®, Noxema®, Suave®, Kate Somerville® and the like are especially preferred for use with the FDAC of this invention.

Typically, the end use compositions will comprise from 0.01 to 15%, and preferably from 14 to 12%, and most preferably, from 1 to 10% by weight active, including all ranges subsumed therein.

The Examples provided are to facilitate an understanding of the invention. They are not intended to limit the scope of the claims.

EXAMPLES

Example 1

FDAC emulsion precursors were prepared by mixing the ingredients identified below in Table I under conditions of moderate shear and ambient temperature. Pressure was atmospheric.

TABLE I

| Ingredient[1] | Sample 1 | Sample 2 | Sample 3 | Sample 4 |
|---|---|---|---|---|
| Water | Balance | Balance | Balance | Balance |
| Maltodextrin | 10 | 10 | 10 | 10 |
| Tween ® 40 | 1 | 1 | 1 | 1 |
| Xanthan gum | 0.3 | 0.3 | 0.3 | 0.3 |
| Carboxymethylcellulose | 0.7 | 0.7 | 0.7 | 0.7 |
| Caprylic capric triglyceride | 10 | — | 10 | 10 |
| Isopropyl Stearate | — | 10 | — | — |
| Retinyl propionate | 1 | 1 | 1 | 1 |
| Phenoxyethanol | — | — | 1.2 | 0.3 |
| Climbazole | — | — | 0.75 | 0.2 |

[1]all in weight percent based on total weight of the FDAC emulsion precursor

The above-identified FDAC emulsion precursors were frozen by shell freezing in a round bottom flask placed in an acetone and dry ice mix (about 50% by weight dry ice) for 20-30 minutes. The resulting frozen emulsions were subjected to a laboratory freeze dryer set at 25° C. to produce FDAC having 3-5% by weight water.

The freeze dried products were subsequently placed in an environmental chamber set at 45° C. for 2 days. The amount of retinyl propionate remaining in the freeze dried composition was determined by a standard reverse phase HPLC methodology.

TABLE 2

| | Sample 1 | Sample 2 | Sample 3 | Sample 4 |
|---|---|---|---|---|
| % RP remaining | PV = 0.4 meq/kg | PV = 13.9 meq/kg | PV = 0.4 meq/kg | PV = 0.4 meq/kg |
| 2 days@45° C. | 101% | 85% | 80% | 86% |

PV = peroxide value for oil

The results unexpectedly illustrate the importance of the oil with low peroxide value. Sample 3 illustrates the detrimental effect of having more than 0.5% by weight hydroxylated solvent oil on stability of retinyl propionate.

Example 2

FDAC emulsion precursors were prepared by mixing the ingredients identified below in Table III under conditions of moderate shear and ambient temperature. Pressure was atmospheric.

TABLE III

| Ingredient[1] | Sample 5 | Sample 6 | Sample 7 | Sample 8 |
|---|---|---|---|---|
| Water | Balance | Balance | Balance | Balance |
| Maltodextrin | 10 | 10 | 10 | 10 |
| Tween 40 | 1 | 1 | 1 | 2 |
| Xanthan gum | 0.3 | 0.3 | 0.3 | 0.3 |
| Carboxymethyl cellulose | 0.7 | 0.7 | 0.7 | 0.7 |
| Caprylic capric triglyceride (CCT) | 0 | 5 | 10 | 20 |
| Retinyl propionate | 1 | 1 | 1 | 1 |

[1]all in weight percent based on total weight of the FDAC emulsion precursor

The above-identified FDAC emulsion precursors were frozen by shell freezing in a round bottom flask placed in an acetone dry ice mix (about 50% by weight dry ice) for 20-30 minutes. The resulting frozen emulsions were subjected to a laboratory freeze dryer set at 25° C. to produce FDAC having 3-5% by weight water.

The freeze dried product was then placed in an environmental chamber set at 45° C. for 2 days. The amount of retinyl propionate remaining in the freeze dried composition was determined by standard reverse phase HPLC methodology.

TABLE IV

| % RP recovered | Sample 5 0% CCT | Sample 6 5% CCT | Sample 7 10% CCT | Sample 8 20% CCT |
|---|---|---|---|---|
| 2 days at 45° C. | 0 | 89 | 100 | 99 |

The results in Table IV illustrate the importance of the oil to active ratio. The higher ratio unexpectedly yields more stable product having more active.

Example 3

FDAC emulsion precursors were prepared by mixing the ingredients identified below in Table V under conditions of moderate shear and ambient temperature. Pressure was atmospheric.

TABLE V

| Ingredient | Sample 9 | Sample 10 |
|---|---|---|
| Water | Balance | Balance |
| Maltodextrin | 10 | 10 |
| Tween 40 | 1 | 1 |
| Xanthan gum | 0.3 | 0.7 |
| Carboxymethylcellulose | 0.7 | 0.3 |
| Caprylic/capric triglyceride | 10 | |
| Benzyl alcohol | | 10 |
| 4-hexyl resorcinol | 1 | 1 |

[1]all in weight percent based on total weight of the FDAC emulsion precursor

The above-identified FDAC emulsion precursors were frozen by shell freezing in a round bottom flask placed in an acetone and dry ice mix (about 50% by weight dry ice) for 20-30 minutes. The resulting frozen emulsions were subjected to a laboratory freeze dryer set at 25° C. to produce FDAC having 3-5% by weight water.

The freeze dried product was then placed in an environmental chamber set at 45° C. for 1 day. The amount of 4-hexylresorcinol remaining in the freeze dried composition was determined by a standard reverse phase HPLC methodology.

TABLE VI

| % 4-Hexylresorcinol remaining | Sample 9 | Sample 10 |
|---|---|---|
| 1 day@45° C. | 96.6 | 88.8 |
| 1 day @70° C. | 99.4 | 81.6 |

The results in Table VI unexpectedly illustrate the detrimental effect of the hydroxylated oil (benzyl alcohol) on active in FDAC.

Example 4

FDAC emulsion precursors were prepared by mixing the ingredients identified below in Table VII under conditions of moderate shear and ambient temperature. Pressure was atmospheric.

TABLE VII

| Ingredient | Sample 11 | Sample 12 | Sample 13 | Sample 14 |
|---|---|---|---|---|
| Water | Balance | Balance | Balance | Balance |
| Maltodextrin | 10.0 | 10.0 | 10.0 | 10.0 |
| Tween 40 | 1.0 | 1.0 | 1.0 | 2.0 |
| Xanthan gum | 0.3 | 0.3 | 0.3 | 0.3 |
| Carboxymethylcellulose | 0.7 | 0.7 | 0.7 | 0.7 |
| Retinyl propionate | 1.0 | 1.0 | 1.0 | 1.0 |
| 4-Hexyl resorcinol | 1.0 | 1.0 | 1.0 | 1.0 |
| Caprylic capric triglyceride | 0 | 10.0 | 20.0 | 0 |
| Benzyl alcohol | 0 | 0 | 0 | 10 |

The above-identified FDAC emulsion precursors were frozen by shell freezing in the round bottom flask placed in an acetone and dry ice mix (50% by weight dry ice) for 20-30 minutes. The resulting frozen emulsions were subjected to a laboratory freeze dryer set at 25° C. to produce FDAC having 3-5% by weight water.

The freeze dried product was then placed in an environmental chamber at 45° C. for up to 5 days. The amount of 4-hexylresorcinol remaining in the freeze dried composition was determined by reverse phase HPLC methodology

TABLE VIII

| | % Retinyl Propionate remaining | | | | % 4-hexylresorcinol remaining | | | |
|---|---|---|---|---|---|---|---|---|
| | Sample 11 | Sample 12 | Sample 13 | Sample 14 | Sample 11 | Sample 12 | Sample 13 | Sample 14 |
| 1 day at 45° C. | 3% | 97% | 100% | 12% | — | — | — | 65% |
| 5 days at 45° C. | 0% | 28% | 83% | 0.6% | 37% | 62% | 95% | 49% |
| 1 day at 70° C. | 0% | 34% | 81% | 0% | — | — | — | 69% |
| 5 days at 70° C. | 0% | 5% | 11% | 0% | 35% | 55% | 60% | 42% |

The results unexpectedly illustrate the importance of the oil to active ratio and the detrimental effect of hydroxylated oil on the stability of active in the FDAC.

Example 5

A consumer in possession of commercially available end use composition may be instructed to combine about 2 to 5 mL of such product with FDAC of the present invention in order to boost the efficacy of the end use composition. The instructions will include an amount of FDAC to use. The consumer may be instructed to combine the end use composition and FDAC in his or her hands and shear the two by rubbing/mixing in the hands prior to application to the body or simultaneously shearing the resulting mixture when applying the mixture to the body.

The invention claimed is:
1. A freeze dried active composition comprising:
  (a) active;
  (b) oil comprising capric caprylic triglyceride;
  (c) less than 6.5% by weight of the composition, water;
  (d) 0.5 to 20% emulsifier; and
  (e) thickening agent
  wherein from 4 to 25 times more oil by weight is present than active in the composition, the oil having a peroxide value from 0 to 4 meq/kg and a polarity index of from 0.1 to 80 mN/m, and less than 0.5% by weight of the total weight of oil is hydroxylated and wherein the active is retinoic acid precursor represented by the formula

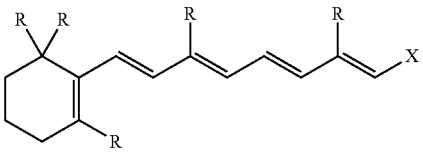

where each R is independently a hydrogen or a $C_{1-6}$ alkyl group and X is

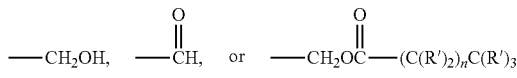

and further where each R' is hydrogen or a $C_1$-$C_3$ alkyl and n is an integer from 0 to 16, the active comprising retinyl propionate, retinyl palmitate or a mixture thereof and the freeze dried active composition is a freeze dried water continuous emulsion.

2. The freeze dried active composition according to claim 1 wherein the composition comprises thickener, from 0.001 to 3.85% by weight water, and oil having a peroxide value from 0.0 to 3.5 and a polarity index from 1.0 to 75 mN/m.

3. The freeze dried active composition according to claim 1 wherein the emulsifier has an HLB from 7 to 18.

4. The freeze dried active composition according to claim 1 wherein the composition is suitable to be combined with water.

5. A method for boosting the performance of an end use composition comprising the steps of:
  (a) combining an end use composition with the freeze dried active composition of claim 1; and
  (b) shearing the end use composition and the freeze dried active composition to produce an enhanced performance end use composition, the end use composition comprising a resorcinol.

6. The method according to claim 5 wherein shearing occurs in hands of a consumer and the freeze dried active composition further comprises an active which is a resorcinol derivative and the end use composition comprises a retinoic acid precursor and the end use composition is an oil-in-water emulsion.

7. The method according to claim 5 wherein the thickening agent in the freeze dried active composition comprises cellulose microfibrils.

8. The method according to claim 5 wherein the end use composition comprises a water soluble active.

9. The method according to claim 8 wherein the water soluble active is niacinamide.

10. The method according to claim 5 wherein the freeze dried active composition further comprises vitamin C.

11. The freeze dried active composition according to claim 1 wherein the composition comprises cellulose microfibrils as a thickening agent.

12. The freeze dried active composition according to claim 11 wherein the cellulose microfibrils include primary cell wall material, secondary cell wall material, bacterial cellulose or a mixture thereof.

13. The freeze dried active composition according to claim 1 wherein the active further comprises a resorcinol and the retinoic acid precursor and resorcinol are present at a weight ratio from 1:0.25 to 0.25 to 1.

14. The freeze dried active composition according to claim 1 wherein oil makes up from 6 to 50% by weight of the composition.

15. The freeze dried active composition according to claim 1 wherein the oil is at least 50% by weight capric caprylic triglyceride based on total weight of oil in the composition, and 5 to 25 times more oil than active is present in the composition.

16. The freeze dried active composition according to claim 15 wherein the freeze dried active composition further comprises 4-ethyl resorcinol, 4-hexyl resorcinol or a mixture thereof.

17. The freeze dried active composition according to claim 1 wherein the oil is at least 75% by weight capric caprylic triglyceride based on total weight of oil in the composition.

18. The freeze dried active composition according to claim 1 wherein the oil is 100% by weight capric caprylic triglyceride based on total weight of oil in the composition.

19. The freeze dried active composition according to claim 1 wherein the composition further comprises climbazole, farnesol, ursolic acid, myristic acid, geranyl geraniol, oleyl betaine, cocoyl hydroxyethyl imidazoline, hexanoyl sphingosine, 12-hydroxystearic acid, petroselinic acid, conjugated linoleic acid, terpineol, thymol or a mixture thereof.

* * * * *